(12) United States Patent
Hayashi et al.

(10) Patent No.: US 7,887,690 B2
(45) Date of Patent: Feb. 15, 2011

(54) DNA SEPARATION DEVICE, DNA SEPARATION METHOD, AND LIGAND DNA

(75) Inventors: Miho Hayashi, Ehime (JP); Kazuyoshi Mori, Ehime (JP); Mizuo Maeda, Tokyo (JP)

(73) Assignee: Panasonic Corporation, Osaka (JP)

( * ) Notice: Subject to any disclaimer, the term of this patent is extended or adjusted under 35 U.S.C. 154(b) by 1148 days.

(21) Appl. No.: 11/585,939

(22) Filed: Oct. 25, 2006

(65) Prior Publication Data

US 2007/0138013 A1    Jun. 21, 2007

(30) Foreign Application Priority Data

Oct. 26, 2005    (JP) .............................. 2005-311933

(51) Int. Cl.
*G01N 27/26*    (2006.01)
*G01N 33/48*    (2006.01)

(52) U.S. Cl. .......................... 204/601; 204/451; 436/94; 536/24.3

(58) Field of Classification Search ................. 204/601, 204/451, 545; 205/792; 536/22.1, 23.1, 536/24.3, 24.31, 24.32; 436/63, 94
See application file for complete search history.

(56) References Cited

U.S. PATENT DOCUMENTS 6,238,927 B1 *    5/2001    Abrams et al. ................. 436/94

FOREIGN PATENT DOCUMENTS

JP    2002-340858    11/2002

\* cited by examiner

*Primary Examiner*—Nam X Nguyen
*Assistant Examiner*—J. Christopher Ball
(74) *Attorney, Agent, or Firm*—Wenderoth, Lind & Ponack, LLP

(57) ABSTRACT

A ligand DNA including a probe portion having a sequence that is complementary to a target DNA to be detected in a sample DNA, and a probe portion having a base sequence that is complementary to a base sequence of a marker DNA 2 in a conjugate DNA 10 is formed, and the sample DNA and the ligand DNA are combined to form a DNA complex, and further, the DNA complex is made to perform electrophoresis in the conjugate DNA. Therefore, it is possible to provide a DNA separation detection method which can appropriately separate the sample DNA and deal with various kinds of target sample DNAs in short time, without the necessity of searching for an optimum electrophoresis condition by complicatedly combining the amount of a bonding control agent to be contained in the conjugate DNA, the viscosity of linear polymer, the amount of the sample DNA, the amount of the conjugate DNA, and the like, for each DNA sequence as a detection target, when separating the sample DNA by electrophoresis.

9 Claims, 8 Drawing Sheets

Fig.9(a)

```
SEQUENCE LISTING

<110> Matsushita Electric Industrial Co., Ltd.

<120> DNA Detection Method, and DNA Detection Apparatus

<160> 10

<210> 1
<211> 7
<212> DNA
<213> Homo sapiens

<400> 1
atcgcgt   7

<210> 2
<211> 7
<212> DNA
<213> Homo sapiens

<400> 2
acgcgat   7

<210> 3
<211> 7
<212> DNA
<213> Homo sapiens

<400> 3
atcgcgt   7

<210> 4
<211> 7
<212> DNA
<213> Homo sapiens

<400> 4
atcacgt   7

<210> 5
<211> 7
<212> DNA
<213> Homo sapiens

<400> 5
acgcgat   7

<210> 6
<211> 6
<212> DNA
<213> Homo sapiens

<400> 6
accagc   6

<210> 7
<211> 12
<212> DNA
<213> Homo sapiens

<400> 7
cttcggctgggg   12

<210> 8
<211> 12
<212> DNA
<213> Homo sapiens

<400> 8
cttcggttgggg   12

```
SEQUENCE LISTING

<212> DNA
<213> Homo sapiens

<400> 9
ccccagccgaaggctggt   18

<210> 10
<211> 18
<212> DNA
<213> Homo sapiens

<400> 10
ccccaaccgaagggcaat   18

<210> 11
<211> 14
<212> DNA
<213> Homo sapiens

<400> 11
cggctgggggctga   14

<210> 12
<211> 14
<212> DNA
<213> Homo sapiens

<400> 12
cggttggggactga   14

<210> 13
<211> 6
<212> DNA
<213> Homo sapiens

<400> 13
cacggt   6

<210> 14
<211> 18
<212> DNA
<213> Homo sapiens

<400> 14
cagcccccagccaccgtg   18

<210> 15
<211> 18
<212> DNA
<213> Homo sapiens

<400> 15
cagtccccaacctcgatg   18
```

DNA SEPARATION DEVICE, DNA SEPARATION METHOD, AND LIGAND DNA

FIELD OF THE INVENTION

The present invention relates to a DNA separation device and a DNA separation method for detecting a difference in portions of base sequences of DNAs, and a ligand DNA.

BACKGROUND OF THE INVENTION

In recent years, with rapid progress of chemical biology, the involvement of genes in various diseases has been understood with a fair degree of precision, and medical cares targeted at genes have attracted attention.

With respect to DNA, currently, SNPs (which is an abbreviation of single nucleotide polymorphisms, and a general term for a difference of a single code (single base) in genes) attract attention. The reason is as follows. By classifying SNPs, it is possible to predict the prevalence rates of many diseases, and the effects or sensitivities of individuals to medical agents, and furthermore, it is possible to perform perfect identification of an individual because there absolutely exist no plural human beings having completely the same SNPs on the planet, even parent and child or brothers.

The applicant of the present invention has proposed a gene examination device and a gene examination method for separating a sample DNA utilizing a conjugate DNA, as a method for examining DNAs having different portions in base sequences such as the above-mentioned SNPs (refer to Japanese Published Patent Application No. 2002-340858).

Hereinafter, the conventional method will be described with reference to FIGS. 6 to 8. FIG. 6 is a diagram illustrating the construction of a common capillary electrophoresis device, FIG. 7 is a state diagram in a capillary tube of the capillary electrophoresis device, and FIG. 8 is a diagram illustrating the relationship between a sample DNA and a conjugate DNA in the conventional method.

With reference to FIG. 6, in a capillary electrophoresis device 100, a first container 131 in which a positive electrode 133 is disposed and a second container 132 in which a negative electrode 134 is disposed are connected by a capillary tube 130 that is filled with a conjugate DNA including a buffer solution 11. Then, as shown in FIG. 7, a sample DNA 200 is injected into the capillary tube 130 that is filled with the conjugate DNA including the buffer solution 11. The conjugate DNA 210 is, as shown in FIG. 8, obtained by combining a marker DNA 212 having a base sequence that is complementary to a portion of a base sequence of a target DNA included in the sample DNA 200 directly with a non-electrophoresis material 211 that hardly moves during electrophoresis, such as linear polymer. The sample DNA 200 is obtained by mixing a first sample DNA 201 which includes, in a portion of its base sequence, the target DNA having a base sequence that is complementary to the conjugate DNA 210, and a second sample DNA 202 having a portion of a base sequence that is not complementary to the conjugate DNA.

Thereafter, a voltage is applied to the both electrodes 133 and 134 by a variable power supply 135 to make the sample DNA 200 in the capillary tube 130 perform electrophoresis, and the sample DNA 200 is separated due to a difference in affinities to the conjugate DNA 210 between the first sample DNA 201 and the second sample DNA 202 in the sample DNA 200.

Next, a description will be given of a method for pseudo-immobilizing the conjugate DNA 210 in the capillary tube 130.

Among DNAs, there exist DNA that forms a double strand and DNA that forms a single strand. Among four bases possessed by DNA, i.e., adenine (A), thymine (T), cytosine (C), and guanine (G), A and T, or G and C are easily bonded to each other, and when DNA forms a double strand, A and T, or G and C are paired with each other. Accordingly, when one of DNAs forming a double strand has a base sequence of 5'-ATCGCGT-3', the other DNA has a base sequence of 5'-ACGCGAT-3'.

The conjugate DNA to be used in the conventional capillary electrophoresis device utilizes the above-mentioned complementary relation of DNA in order to separate the sample DNA. That is, as shown in FIG. 8, a DNA sequence that is complementary to the target DNA to be detected in the sample DNA 200 is given to the marker DNA 212 in the conjugate DNA 210.

For example, assuming that the first sample DNA 201 as the target DNA in the sample DNA 200 is mutant DNA, and the DNA sequence of the mutant DNA includes 5'-ATCGCGT-3' while the DNA sequence of the wild DNA as the second sample DNA included in the sample DNA 200 is 5'-ATCACGT-3', a base of the mutant DNA 201 and a base of the wild DNA 202 differ from each other at the underlined portions. At this time, assuming that the sequence of the marker DNA 212 in the conjugate DNA 210 is 5'-ACGCGAT-3', the wild DNA 202 becomes not complementary to the marker DNA 212 in the conjugate DNA 210 at the underlined portion. Thereby, in the sample DNA 200 bonded to the conjugate DNA 210, the entire bonding force of the mutant DNA 201 becomes larger than that of the wild DNA 202, and the mutant DNA 201 moves with a delay from the wild DNA during electrophoresis.

By the way, the above-mentioned DNA sample 200 is formed by extracting DNA from blood or the like by destroying cells, and amplifying a portion including a target DNA sequence by PCR or the like. At this time, while the number of bases of the conjugate DNA 210 is determined according to the number of bases and the base sequence pattern of the portion to be amplified, the number of bases of the target DNA to be amplified by PCR or the like is about 50, in which it is probabilistically considered that the same DNA sequences do not exist, in human genome DNA comprising about three billion of base pairs.

The conjugate DNA 210 is formed as follows. When the non-electrophoresis material 211 is linear polymer made of acrylamide, the 5' end of the marker DNA 212 having a sequence complementary to the target DNA sequence in the sample DNA 200 is vinylated, and the marker DNA 212 is mixed at a predetermined rate into the acrylamide monomer, and further, ammonium persulfate as a polymerization starter and tetramethylethylenediamine as a polymerization agent are mixed thereto, and the resultant solution is left still for two hours.

The conjugate DNA 210 formed as described above is filled in the capillary tube 130 of the conventional capillary electrophoresis device 100, and the sample DNA 200 is injected into the conjugate DNA 210 to make the sample DNA 200 move from the second container 123 to the first container 131 by electrophoresis, whereby interaction between the conjugate DNA 210 and the sample DNA 200 occurs not only in the vicinity of the wall surface of the capillary tube 130 but also inside the capillary tube 130, and the sample DNA 200 can be separated into the wild DNA 202 and the mutant DNA 201 by a difference in movement speeds between the wild DNA 202 and the mutant DNA 201 in the sample DNA 200 that is bonded to the conjugate DNA 210 by the interaction, and consequently, gene abnormality of SNPs can be discriminated easily and accurately in short time.

As described above, the conventional conjugate DNA 210 is constituted such that the end of the marker DNA 212 having a base sequence that is complementary to the base sequence of the target DNA as a detection target in the sample DNA 200 is bonded to the non-electrophoresis material 211, conjugate DNAs as many as the target DNAs are required, and therefore, formation of a conjugate DNA must be carried out from the beginning every time the detection target changes, resulting in an immense amount of time until the result of measurement is obtained.

Further, the separation performance of the conventional conjugate DNA 210 is determined by the bonding force of the complementary hydrogen bonding with the sample DNA, the bonding force of the marker DNA 212 and the sample DNA 200 varies depending on the length or the sequence pattern of the base sequence of the marker DNA 212 in the conjugate DNA 210, and therefore, it is necessary to search for various conditions for appropriately separating the sample DNA 200, every time the base sequence of the target DNA in the sample DNA 200 changes.

To be specific, among the four bases of DNA, adenine (A) and thymine (T) are paired while cytosine (C) and guanine (G) are paired as described above, and adenine (A) and thymine (T) are bonded by two hydrogen bonds while cytosine (C) and guanine (G) are bonded by three hydrogen bonds. Accordingly, even when the length of the marker DNA 212 is constant, the bonding force of the sample DNA 200 and the marker DNA 212 varies depending on the sequence pattern of the sample DNA 200. For example, when the base sequence of the marker DNA 212 as the complementary bonding portion comprises 6 bases, there exist 12 hydrogen bonds at minimum (all A-T bonds) to 18 hydrogen bonds at maximum (all C-G bonds), and therefore, the bonding force varies very much even when the length of the base sequence of the complementary bonding portion is constant.

However, when performing separation of the sample DNA 200 by electrophoresis, the items that can be controlled after preparation of the conjugate DNA 210 on the device 100 side are only the voltage during electrophoresis and the measurement temperature, and such control on the device 100 side has a limitation in controlling the bonding force of the sample DNA 200 and the marker DNA 212 in the conjugate DNA 210. In order to solve this problem, conventionally, the conjugate DNA 210 is formed according to the base sequence of the detection target DNA included in the sample DNA 200, whereby the bonding force between the target DNA included in the sample DNA 200 and the marker DNA 212 having the sequence complementary to the target DNA is appropriated.

As a method thereof, for example, the length of the marker DNA 212 in the conjugate DNA 210, which is the complementary bonding portion to the sample DNA, is increased or reduced.

In this method, however, the bonding force between the sample DNA 200 and the marker DNA 212 cannot be minutely controlled.

In order to solve this problem, conventionally, minute control of the bonding force between the sample DNA 200 and the conjugate DNA 210 is realized by controlling, for every sample DNA 200, the amount of the bonding control agent included in the conjugate DNA 210, the viscosity of the non-electrophoresis material 211, the amount of the sample DNA 200, or the amount of the conjugate DNA 210.

The electrophoresis speed of the sample DNA 200 becomes slower as the amount of the bonding control agent is larger, the viscosity of the non-electrophoresis material 211 is higher, the amount of the conjugate DNA 210 is larger, the voltage during electrophoresis is lower, and the measurement temperature is lower, and thereby the bonding force between the sample DNA 200 and the conjugate DNA 210 in the hermetically sealed flow path is increased.

However, as described above, it requires an immense amount of labor and time to estimate various patterns in which the amount of the bonding control agent included in the conjugate DNA, the viscosity of the non-electrophoresis material 211, the amount of the sample DNA 200, and the amount of the conjugate DNA 210 are complicatedly combined for each sample. DNA, and search for an optimum electrophoresis condition by examination.

SUMMARY OF THE INVENTION

The present invention is made to solve the above-mentioned problems and has for its object to provide a DNA separation device and a DNA separation method which can separate a sample DNA appropriately in short time, and can deal with various kinds of target sample DNAs, without the necessity of searching for an optimum electrophoresis condition by complicatedly combining the amount of a bonding control agent to be contained in the conjugate DNA, the viscosity of linear polymer, the amount of the sample DNA, the amount of the conjugate DNA, and the like, for each DNA sequence as a detection target in the sample DNA, when separating the sample DNA by electrophoresis.

In order to solve the above-mentioned problems, according to the present invention, there is provided a DNA separation device for separating, by electrophoresis, a first sample DNA including a first base sequence, and a second sample DNA including a second base sequence that is partially different from the first base sequence, which are contained in a sample solution, wherein a positive electrode and a negative electrode are provided on end portions at both ends of a capillary type hermetically-sealed flow path, respectively, so that the electrodes are immersed in a buffer solution; a conjugate DNA solution which is obtained by adding, in a buffer solution, a conjugate DNA that is obtained by combining a marker DNA having a specific base sequence with a non-electrophoresis material which performs electrophoresis at a speed that is negligible low relative to the electrophoresis speeds of the first sample DNA and the second sample DNA, is filled in the hermetically-sealed flow path; a presample solution including a first DNA complex which is obtained by combining the first sample DNA with a first ligand DNA that includes a first probe having a base sequence complementary to the first base sequence, and a second probe having a base sequence complementary to the base sequence of the marker DNA, and a second DNA complex which is obtained by combining the second sample DNA with a second ligand DNA that includes a third probe having a base sequence complementary to the second base sequence, and a fourth probe having a base sequence that is at least one base different from the base sequence of the second probe, is injected into the hermetically-sealed flow path; and voltage is applied to the positive electrode and the negative electrode to make the first DNA complex and the second DNA complex perform electrophoresis in the conjugate DNA solution, thereby separating the DNA complexes.

Therefore, it is possible to separate the first and second DNA complexes by changing the base sequence of the ligand DNA to be bonded to the sample DNA, without the necessity of changing the base sequence of the conjugate DNA every time the base sequence of the target DNA to be detected in the sample DNA changes, or searching for the electrophoresis condition of the conjugate DNA having appropriate length and bonding force, thereby providing a DNA separation device which can determine whether SNPs exist or not, accurately in short time.

Further, according to the present invention, there is provided a DNA separation device for separating, by electrophoresis, a first sample DNA including a first base sequence, and a second sample DNA including a second base sequence that is partially different from the first base sequence, which are contained in a sample solution, wherein a positive electrode and a negative electrode are provided on end portions at both ends of a capillary type hermetically-sealed flow path, respectively, so that the electrodes are immersed in a buffer solution; a conjugate DNA solution which is obtained by adding, in a buffer solution, a conjugate DNA that is obtained by combining a marker DNA having a specific base sequence with a non-electrophoresis material which performs electrophoresis at a speed that is negligible low relative to the electrophoresis speeds of the first sample DNA and the second sample DNA, is filled in the hermetically-sealed flow path; a presample solution including a first DNA complex which is obtained by combining the first sample DNA with a first ligand DNA that includes a first probe having a base sequence complementary to the first base sequence, and a second probe having a base sequence complementary to the base sequence of the marker DNA, and a third DNA complex which is obtained by combining the second sample DNA with a third ligand DNA that includes a third probe having a base sequence complementary to the second base sequence, is injected into the hermetically-sealed flow path; and voltage is applied to the positive electrode and the negative electrode to make the first DNA complex and the third DNA complex perform electrophoresis in the conjugate DNA solution, thereby separating the DNA complexes.

Therefore, it is possible to separate the first and second DNA complexes by changing the base sequence of the ligand DNA to be bonded to the sample DNA, without the necessity of changing the base sequence of the conjugate DNA every time the base sequence of the target DNA to be detected in the sample DNA changes, or searching for the electrophoresis condition of the conjugate DNA having appropriate length and bonding force, thereby providing a DNA separation device which can determine whether SNPs exist or not, accurately in short time.

Further, the DNA separation device according to the present invention further includes a detector for detecting at least one of the first sample DNA and the second sample DNA which move in the hermetically-sealed flow path by electrophoresis; the conjugate DNA solution is filled in the hermetically-sealed flow path, and the presample solution including at least one of the first DNA complex and the second DNA complex is injected into the hermetically-sealed flow path; and voltage is applied to the positive electrode and the negative electrode to make the first DNA complex or the second DNA complex included in the presample solution perform electrophoresis in the conjugate DNA solution, and at least one of the first DNA complex and the second DNA complex is detected by the detector.

Further, the DNA separation device according to the present invention further includes a detector for detecting at least one of the first sample DNA and the second sample DNA which move in the hermetically-sealed flow path by electrophoresis; the conjugate DNA solution is filled in the hermetically-sealed flow path, and the presample solution including at least one of the first DNA complex and the third DNA complex is injected into the hermetically-sealed flow path; and voltage is applied to the positive electrode and the negative electrode to make the first DNA complex or the third DNA complex included in the presample solution perform electrophoresis in the conjugate DNA solution, and at least one of the first DNA complex and the third DNA complex is detected by the detector.

Therefore, it is possible to detect the first sample DNA or the second sample DNA which is included in the sample solution.

Further, in the DNA separation device according to the present invention, a fluorescence dye is applied to the first sample DNA or the second sample DNA.

Therefore, it is possible to detect only the first sample DNA or the second sample DNA from among various DNAs included in the solution in the hermetically-sealed flow path, by detecting the fluorescence dye.

Further, in the DNA separation device according to the present invention, each of the first probe and the third probe comprises ten bases or more.

Therefore, it is possible to form the DNA complex by firmly bonding the sample DNA to the ligand DNA.

Further, in the DNA separation device according to the present invention, the second probe or the fourth probe comprises six bases or more.

Therefore, it is possible to appropriately delay the electrophoresis speed of the DNA complex by appropriately bonding the DNA complex and the conjugate DNA.

Further, in the DNA separation device according to the present invention, the buffer solution is one selected from a group consisting of a TB buffer solution, a Tris-HCl buffer solution, a TAE buffer solution, and a TBE buffer solution.

Further, in the DNA separation device according to the present invention, the non-electrophoresis material is a linear polymer made of acrylamide or ethylene glycol.

Further, according to the present invention, there is provided a DNA separation method for separating, by electrophoresis, a first sample DNA including a first base sequence, and a second sample DNA including a second base sequence that is partially different from the first base sequence, which are contained in a sample solution, and the method comprises a filling step of filling a hermetically-sealed flow path with a conjugate DNA solution which is obtained by adding, in a buffer solution, a conjugate DNA that is obtained by combining a marker DNA with a non-electrophoresis material which performs electrophoresis at a speed that is negligible low relative to the electrophoresis speeds of the first sample DNA and the second sample DNA; a presample solution formation step of mixing and hybridizing the sample solution with a first ligand DNA that includes a first probe having a base sequence complementary to the first base sequence, and a second probe having a base sequence different from the first and second base sequences, and a second ligand DNA that includes a third probe having a base sequence complementary to the second base sequence, and a fourth probe having a base sequence that is at least one base different from the base sequence of the second probe, thereby forming a presample solution including a first DNA complex obtained by combining the first sample DNA with the first ligand DNA, and a second DNA complex obtained by combining the second sample DNA with the second ligand DNA; an injection step of injecting the presample solution formed in the presample solution formation step into the hermetically-sealed flow path that is filled with the conjugate DNA solution in the filling step; and a separation step of applying a predetermined voltage to a positive electrode and a negative electrode disposed at both ends of the hermetically-sealed flow path to make the first DNA complex and the second DNA complex perform electrophoresis, thereby separating the DNA complexes.

Therefore, it is possible to separate the first and second DNA complexes by a difference in bonding forces between the conjugate DNA filled in the hermetically-sealed flow path, and the first and second DNA complexes which are obtained by combining the first and second sample DNAs with the first and second ligand DNAs having, in portions thereof, base sequences complementary to the respective sample DNAs, and consequently, it is possible to determine whether SNPs exist or not, accurately in short time.

Further, according to the present invention, there is provided a DNA separation method for separating, by electrophoresis, a first sample DNA including a first base sequence, and a second sample DNA including a second base sequence that is partially different from the first base sequence, which are contained in a sample solution, and the method comprises a filling step of filling a hermetically-sealed flow path with a conjugate DNA solution which is obtained by adding, in a buffer solution, a conjugate DNA that is obtained by combining a marker DNA with a non-electrophoresis material which performs electrophoresis at a speed that is negligible low relative to the electrophoresis speeds of the first sample DNA and the second sample DNA; a presample solution formation step of mixing and hybridizing the sample solution with a first ligand DNA that includes a first probe having a base sequence complementary to the first base sequence, and a second probe having a base sequence different from the first and second base sequences, and a third ligand DNA that includes a third probe having a base sequence complementary to the second base sequence, thereby forming a presample solution including a first DNA complex obtained by combining the first sample DNA with the first ligand DNA, and a third DNA complex obtained by combining the second sample DNA with the third ligand DNA; an injection step of injecting the presample solution formed in the presample solution formation step into the hermetically-sealed flow path that is filled with the conjugate DNA solution in the filling step; and a separation step of applying a predetermined voltage to a positive electrode and a negative electrode disposed at both ends of the hermetically-sealed flow path to make the first DNA complex and the third DNA complex perform electrophoresis, thereby separating the DNA complexes.

Therefore, the first and second sample DNAs are specifically bonded to the first and third ligand DNAs having the complementary sequences to form the DNA complexes, and the first and third DNA complexes can be separated by a difference in bonding forces between the first and third DNA complexes, and the conjugate DNA filled in the hermetically-sealed flow path, and consequently, it is possible to determine whether SNPs exist or not, accurately in short time.

Further, the DNA separation method according to the present invention comprises the presample solution formation step of mixing and hybridizing the first ligand DNA, the second ligand DNA, and the sample solution including at least one of the first sample DNA and the second sample DNA, thereby forming a presample solution including at least one of the first DNA complex and the second DNA complex; the injection step of injecting the presample solution into the hermetically-sealed flow path filled with the conjugate DNA solution; and a detection step of applying a predetermined voltage to the positive electrode and the negative electrode to make the first DNA complex or the second DNA complex included in the presample solution perform electrophoresis in the conjugate DNA solution, and detecting at least one of the first DNA complex and the second DNA complex that move in the hermetically-sealed flow path.

Further, in the DNA separation method according to the present invention comprises the presample solution formation step of mixing and hybridizing the first ligand DNA, the third ligand DNA, and the sample solution including at least one of the first sample DNA and the second sample DNA, thereby forming a presample solution including at least one of the first DNA complex and the third DNA complex; the injection step of injecting the presample solution into the hermetically-sealed flow path filled with the conjugate DNA solution; and a detection step of applying a predetermined voltage to the positive electrode and the negative electrode to make the first DNA complex or the third DNA complex included in the presample solution perform electrophoresis in the conjugate DNA solution, and detecting at least one of the first DNA complex and the third DNA complex that move in the hermetically-sealed flow path.

Therefore, it is possible to detect the first sample DNA or the second sample DNA which is included in the sample solution.

Further, according to the present invention, there is provided a first ligand DNA to be bonded to a first sample DNA when the first sample DNA including a first base sequence and a second sample DNA including a second base sequence that is partially different from the first base sequence, which are included in a sample solution, are made to perform electrophoresis in a conjugate DNA to separate the sample DNAs, and the first ligand DNA comprises a synthetic oligo including a first probe having a base sequence that is complementary to the first base sequence of the first sample DNA, and a second probe having a base sequence that is complementary to a marker DNA in a conjugate DNA which is obtained by combining the marker DNA having a specific base sequence with a non-electrophoresis material which performs electrophoresis at a speed that is negligible low relative to the electrophoresis speeds of the respective sample DNAs.

Therefore, even when the sequence of the conjugate DNA is made constant, it is possible to deal with various kinds of samples by changing the sequence of a region to be bonded to the sample, in the first ligand DNA.

Further, according to the present invention, there is provided a second ligand DNA to be bonded to a second sample DNA when a first sample DNA including a first base sequence and the second sample DNA including a second base sequence that is partially different from the first base sequence, which are included in a sample solution, are made to perform electrophoresis in a conjugate DNA to separate the sample DNAs, and the second ligand DNA comprises a synthetic oligo including a third probe having a base sequence that is complementary to the second base sequence of the second sample DNA, and a fourth probe having a base sequence at least one base of which is not complementary to a marker DNA in a conjugate DNA which is obtained by combining the marker DNA having a specific base sequence with a non-electrophoresis material which performs electrophoresis at a speed that is negligible low relative to the electrophoresis speeds of the respective sample DNAs.

Therefore, even when the sequence of the conjugate DNA is made constant, it is possible to deal with various kinds of samples by changing the sequence of a region to be bonded to the sample, in the second ligand DNA.

Further, according to the present invention, there is provided a third ligand DNA to be bonded to a second sample DNA when a first sample DNA including a first base sequence and the second sample DNA including a second base sequence that is partially different from the first base sequence, which are included in a sample solution, are made to perform electrophoresis in a conjugate DNA to separate the sample DNAs, and the third ligand DNA comprises a synthetic oligo including a third probe having a base sequence that is complementary to the second base sequence of the second sample DNA.

Therefore, even when the sequence of the conjugate DNA is made constant, it is possible to deal with various kinds of samples by changing the sequence of a region to be bonded to the sample, in the third ligand DNA.

BRIEF DESCRIPTION OF THE DRAWINGS

FIG. 9(a) is a reference diagram illustrating a DNA sequence listing.

FIG. 9(b) is a reference diagram illustrating a DNA sequence listing.

EMBODIMENTS OF THE PRESENT INVENTION

Embodiment 1

In a first embodiment of the present invention, a first ligand DNA that can be bonded to both a first sample DNA and a conjugate DNA, and a second ligand DNA that can be bonded to both a second sample DNA and the conjugate DNA are bonded to the first sample DNA and the second sample DNA to create a first DNA complex and a second DNA complex, respectively, and thereafter, the first and second DNA complexes are made to perform electrophoresis in the conjugate DNA to separate these DNA complexes.

Hereinafter, a description will be given of the constructions of the conjugate DNA and the ligand DNAs according to the first embodiment.

Figure 1:
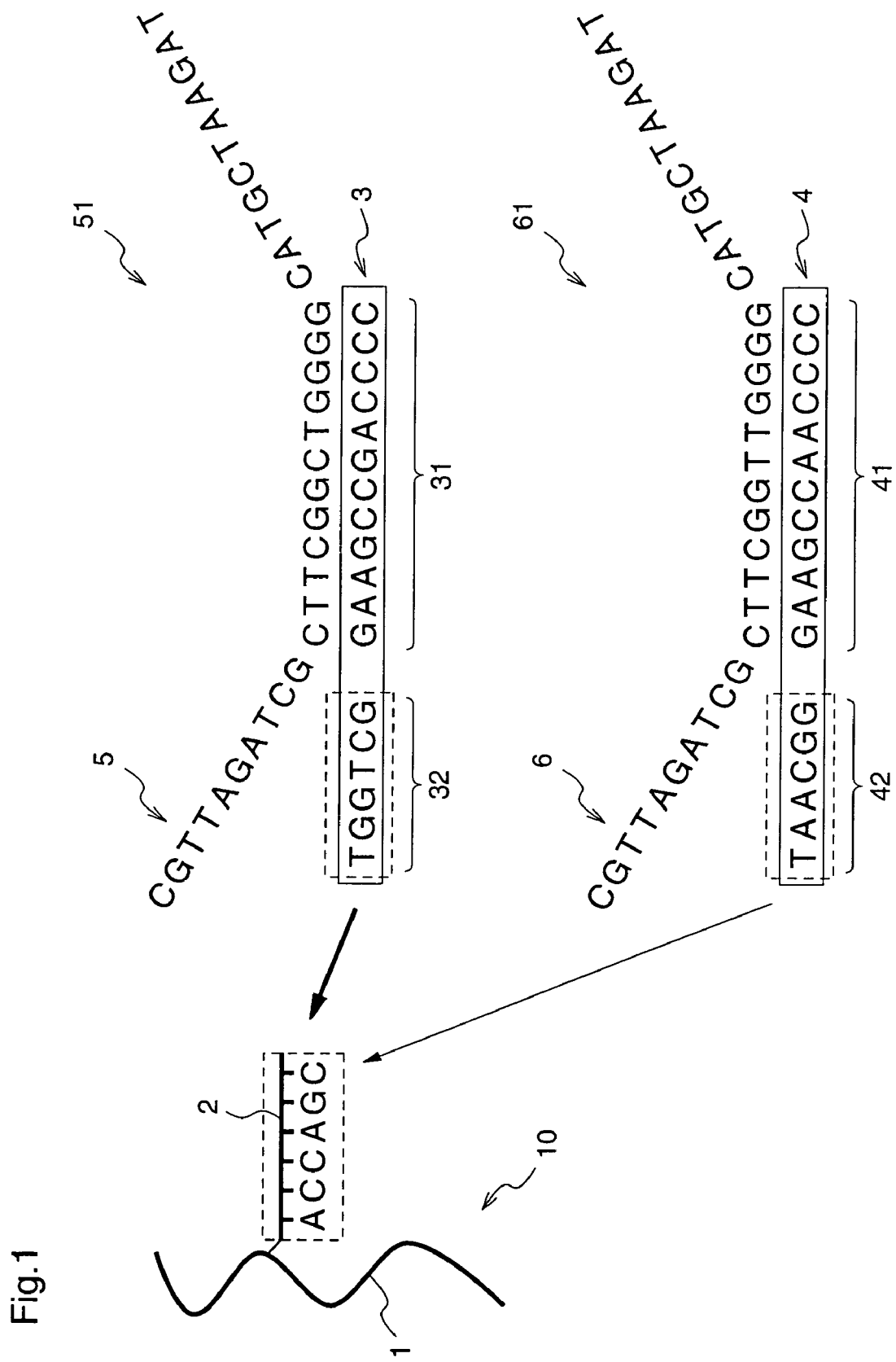
FIG. 1 is a diagram illustrating correlations between a conjugate DNA, and first and second DNA complexes comprising the first and second ligand DNAs and first and second sample DNAs, respectively, according to a firth embodiment of the present invention.

FIG. 1 is a diagram illustrating the correlations among the conjugate DNA, the two sample DNAs included in a sample solution, and the two ligand DNAs, according to the first embodiment.

Initially, the conjugate DNA 10 according to the first embodiment is formed by bonding a non-electrophoresis material 1 and a marker DNA 2 as in the prior art.

The non-electrophoresis material 1 comprises a material which performs electrophoresis at a speed that is negligible low relative to the speed of the sample DNA during electrophoresis. The term "performing electrophoresis at a speed that is negligible low relative to the electrophoresis speed of the sample DNA" means a level in which, when the sample DNA and the conjugate DNA move by electrophoresis in a capillary tube having an inner diameter of 75 μm and a length of 38 cm, the conjugate DNA takes more than 60 minutes while the sample DNA takes only 8 minutes, and it can be said that the conjugate DNA hardly moves during electrophoresis.

The non-electrophoresis material 1 may be any material so long as it hardly moves during electrophoresis, for example, polymer, glass, or magnetic beads may be employed. In this first embodiment, the non-electrophoresis material 1 is polyethylene glycol which is a commonly used linear polymer.

Then, an arbitrary base sequence is set for the marker DNA 2.

When the non-electrophoresis material 1 is polyethylene glycol, the conjugate DNA 10 is formed as follows. The end of the polyethylene glycol is carboxylated, and the carboxylated portion is reacted with N-hydroxysuccinimide to be esterified, while the 5' end of the marker DNA 2 is aminated, and the aminated marker DNA 2 is amide bonded to the esterified polyethylene glycol.

Next, the first and second ligand DNAs according to the first embodiment will be described. In this first embodiment, it is assumed that the first sample DNA included in the sample solution includes a target DNA to be detected.

The first and second ligand DNAs according to the first embodiment are constructed such that a first area (first, third probe) that binds to the sample DNA and a second area (second, fourth probe) that binds to the marker DNA 2 in the conjugate DNA 10 are arranged in a single synthetic oligo, as shown in FIG. 1. Since the first and second ligand DNAs are thus constructed, the first and second ligand DNAs can bind to the first and second sample DNAs and to the conjugate DNA. As a result, even when the base sequence of the sample DNA to be detected changes, it is possible to cope with this change in the sample DNA, not by changing the base sequence of the marker DNA in the conjugate DNA but by changing the base sequence of the first area in the ligand DNA, which binds to the sample DNA, whereby a constant conjugate DNA can be used even when the sample DNA varies in many kinds.

To be specific, the first ligand DNA 3 is a synthetic oligo comprising a first probe 31 having a base sequence complementary to the base sequence of the first sample DNA 5, and a second probe 32 having a base sequence complementary to the base sequence of the marker DNA 2 in the conjugate DNA 10. The second ligand DNA 4 is a synthetic oligo comprising a third probe 41 having a base sequence complementary to the base sequence of the second sample DNA 6, and a fourth probe 42 having a base sequence that is at least one base different from the base sequence of the second probe 32 in the first ligand DNA 3.

For example, assuming that the marker DNA 2 in the conjugate DNA is 5'-CGACCA-3', the sequence of the target DNA to be detected in the first sample DNA 5 is 5'-GGGGTCGGCTTC-3', and the target DNA in the second sample DNA 6 having a base sequence that is partially different from the base sequence of the first sample DNA is 5'-GGGGTTGGCTTC-3', the first ligand DNA 3 is 5'-TG-GTCG-GAAGCCGACCC-3' comprising the first probe 31 having a base sequence complementary to the target DNA in the first sample DNA 5, and the second probe 32 having a base sequence complementary to the marker DNA 2, while the second ligand DNA 4 is 5'-TAACGG-GAAGCCAACCCC-3' comprising the third probe 41 having a base sequence complementary to a portion of the second sample DNA 6, and the fourth probe 42 having a base sequence different from the second probe 32 of the first ligand DNA 3.

As described above, the base sequence of the second probe 32 of the first ligand DNA 3 that binds to the first sample DNA 5 as a detection target is made complementary to the base sequence of the marker DNA 2 in the conjugate DNA 10, and a portion of the base sequence of the fourth probe 42 of the second ligand DNA 4 is made non-complementary to the base sequence of the marker DNA 2, whereby the bonding force between the first ligand DNA 3 and the conjugate DNA 10 becomes larger than the bonding force between the second ligand DNA 4 and the conjugate DNA 10. Therefore, when the first and second ligand DNAs 3 and 4 are moved by electrophoresis in the conjugate DNA, a slight difference can be made in the electrophoresis speeds between the first ligand DNA 3 and the second ligand DNA 4, and the two sample DNAs that bind to the first and second ligand DNAs 3 and 4, respectively, can be separated due to this difference in the electrophoresis speeds.

It is necessary to combine each of the first ligand DNA 3 and the second ligand DNA 4 with either the first sample DNA 5 or the second sample DNA 6. Accordingly, the first and second ligand DNAs 3 and 4 must have such base sequences that no hairpin loop structure is formed by its own base sequences in each ligand.

However, depending on the base sequence of the first sample DNA 5 or the second sample DNA 6 in the sample solution, there is a possibility that the first or second ligand DNA 3 or 4 may have base sequences that form a hairpin loop structure in each ligand. In this case, the base sequence of the second area that binds to the marker DNA 2 in the conjugate DNA 10 in the first or second ligand DNA 3 or 4, i.e., the base sequence of the second probe 32 in the first ligand DNA 3 or the fourth probe 42 in the second ligand DNA 4, is changed, thereby to prevent the first or second ligand DNA 3 or 4 from forming a hairpin loop structure.

However, when the base sequence of the second or fourth probe 32 or 42 in the first or second ligand DNA 3 or 4 is changed, it is necessary to change the sequence of the marker DNA 2 in the conjugate DNA 10 to a sequence that is complementary to the base sequence of the second probe 32.

Further, the lengths of the base sequences of the first probe 31 in the first ligand DNA 3 and the third probe 41 in the second ligand DNA 4 are 10~20 bases, and preferably, about 12 bases.

The reason is as follows. If the length of the base sequence in the first area to be bonded to the sample DNA, of the first or second ligand DNA 3 or 4 (i.e., the base sequence of the first probe 31 or the third probe 41) is too short, after the first and second ligand DNAs 3 and 4 are bonded to the first and second sample DNAs 5 and 6 to form the first and second DNA complexes 5 and 6, respectively, the ligand DNAs might be separated from the sample DNAs because of weak bonding forces thereof. Conversely, if the base sequence in the first area of the first or second ligand DNA 3 or 4 (i.e., the base sequence of the first probe 31 or the third probe 41) is too long, the first and second ligand DNA 3 and 4 cannot recognize the partial difference in the base sequences of the first and second sample DNAs 5 and 6, resulting in a possibility that the ligand DNAs and the sample DNAs might be non-specifically bonded, such as that the first ligand DNA 5 is undesirably bonded to the second sample DNA 4.

Further, the length of the base sequence of the marker DNA 2 in the conjugate DNA 10 is 6~12 bases, and preferably, about 7 bases.

The reason is as follows. If the base sequence of the marker DNA 2 in the conjugate DNA 10 is too short, the bonding force between the conjugate DNA 10 and the first DNA complex 51 in the presample solution becomes too weak, and the electrophoresis speed of the first DNA complex cannot be slowed, leading to a possibility that the sample DNA cannot be appropriately separated. Conversely, if the base sequence of the marker DNA 2 in the conjugate DNA 10 is too long, the bonding force between the conjugate DNA 10 and the first DNA complex 51 in the presample solution becomes too strong, leading to a possibility that the DNA complex remains bonded to the conjugate DNA 10.

Hereinafter, a DNA separation device for separating the first and second sample DNAs 5 and 6 existing in the sample solution by using the above-mentioned first and second ligand DNAs 3 and 4, and the conjugate DNA 10, will be described.

In this first embodiment, a description will be given of the case where, in the sample solution, the first sample DNA as a detection target having a specific sequence, and the second sample DNA having a sequence that is partially different from the specific sequence are separated from each other. It is assumed that the first sample DNA has SNPs (Single Nucleotide Polymorphisms) while the second sample DNA has no SNPs.

Figure 6:
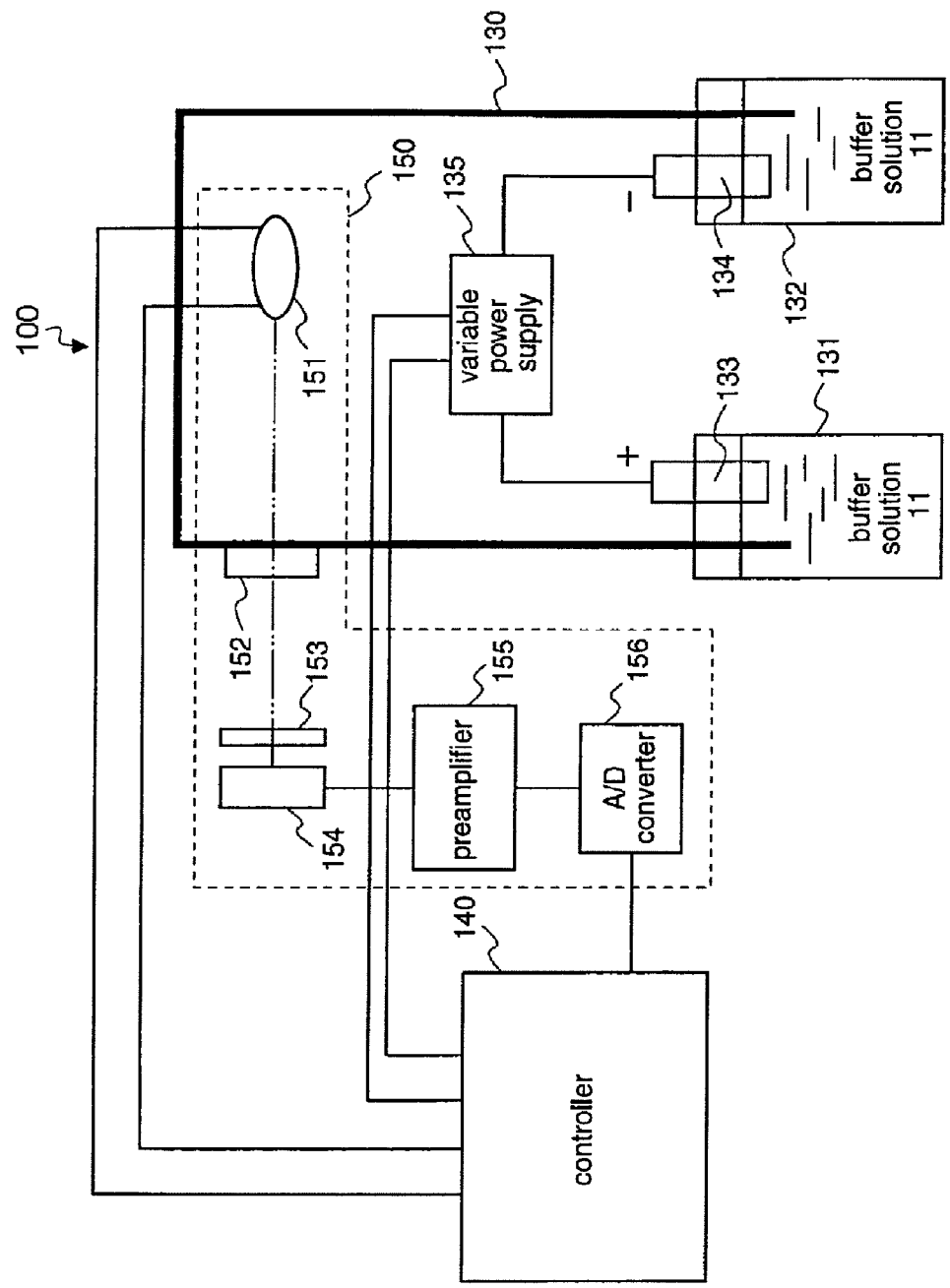
FIG. 6 is a diagram illustrating the construction of a common capillary electrophoresis device.

As a capillary electrophoresis device for separating the sample DNA according to the first embodiment, a common capillary electrophoresis device 100 shown in FIG. 6 will be employed.

The capillary electrophoresis device 100 comprises a capillary tube 130 as a hermetically-sealed flow path for separating the sample DNA, first and second containers 131 and 132 for holding a buffer solution 11 whose pH is adjusted to a predetermined value, and having a buffering function, and also supporting electrolyte, a positive electrode 133 and a negative electrode 134 for applying voltage to the both ends of the capillary tube 130, a variable power supply 135 for applying voltage to the electrodes 133 and 134, a detector 150 for detecting the target DNA in the sample solution, and a controller 140 for controlling the voltage application of the variable power supply 135 or the detector 150.

The detector 150 comprises a laser 151 for emitting excitation light to a fluorescent dye added to the sample solution in the capillary tube 130, a slit 152 for controlling the amount of light to observe luminescence of the fluorescent dye, a filter 153 for cutting only the excitation light in the light that has passed through the slit 152, a photomultiplier 154 for detecting the light that has passed through the filter 153, a preamplifier 155 for electrically amplifying a signal detected by the photomultiplier 154, and an A/D converter 156 for converting the analog signal into a digital signal.

In this first embodiment, it is assumed that the sample solution contains the first sample DNA having a specific sequence as a detection target and the second sample DNA having a sequence that is partially different from the specific sequence, and the first sample DNA has SNPs (Single Nucleotide Polymorphisms) while the second sample DNA has no SNPs, and hereinafter, the case where these two sample DNAs are separated will be described.

Initially, the conjugate DNA 10 in which the marker DNA 2 comprises 6 bases is adjusted such that the DNA concentration is 100 μM, Tris-Boracic acid (TB) buffer is 50 mM, and magnesium chloride is 500 μM, and the adjusted conjugate DNA 10 is filled into the capillary tube 130 having an inner diameter of 100 μm and a total length of 50 cm (effective length=40 cm). The buffer solution 11 is not restricted to the TB buffer. For example, a Tris-HCl buffer solution, a Tris-Acetic acid-EDTA (TAE) buffer solution, or a Tris-Boracic acid-EDTA (TBE) buffer solution may be employed.

Next, the first and second ligand DNAs 3 and 4 are formed.

At this time, the two kinds of ligand DNAs, i.e., the first and second ligand DNAs 3 and 4, should be always prepared. The reason is as follows. Since there are considered three types of sample solutions, i.e., a sample solution in which only the first sample DNA 5 including the first base sequence exists, a sample solution in which only the second sample DNA 6 including the second base sequence exists, and a sample solution in which both of the sample DNAs 5 and 6 are included, the ligand DNA should cope with the sample solution in which any of the sample DNAs having the first and second base sequences exists.

The first and second ligand DNAs 3 and 4 are mixed into the sample solution to be hybridized, thereby forming a presample solution including a DNA complex in which the sample DNA in the sample solution is bonded to the ligand DNA.

To be specific, the first sample DNA 5 having SNPs, the first ligand DNA 3 having a base sequence that is complementary to the first sample DNA 5, the second sample DNA 6 having no SNPs, and the second ligand DNA 4 having a base sequence that is complementary to the second sample DNA 4 are mixed into the sample solution so that the final concentration becomes 5 µM to perform hybridization, thereby forming a presample solution including the first and second DNA complexes 51 and 61.

When only the first sample DNA 5 exists in the sample solution, the presample solution includes the first DNA complex that is obtained by bonding the first sample DNA 5 and the first ligand DNA 3, and the second ligand DNA 4 that exists in its single-stranded state. Further, when only the second sample DNA 6 exists in the sample solution, the presample solution includes the second DNA complex 61 that is obtained by bonding the second sample DNA 6 and the second ligand DNA 4, and the first ligand DNA 3 that exists in its single-stranded state.

Figure 7:
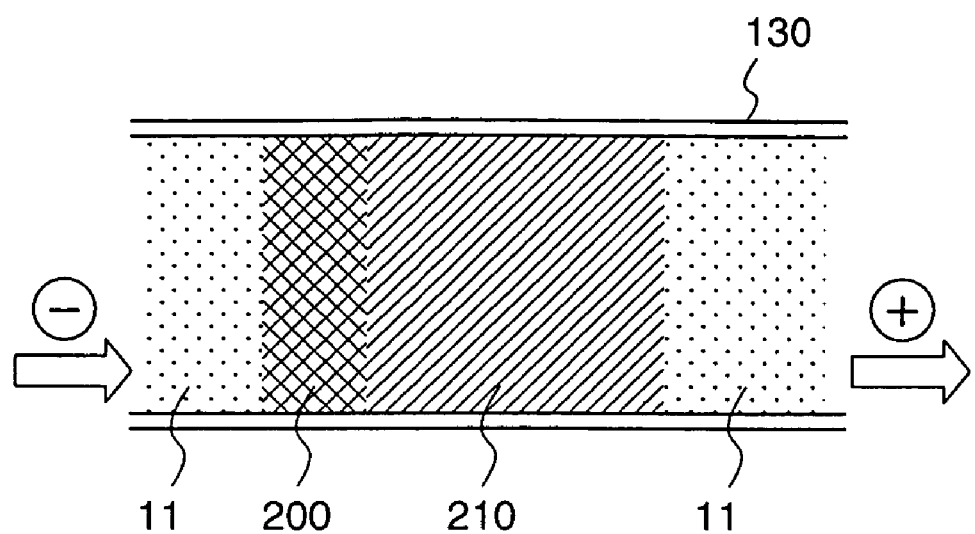
FIG. 7 is a diagram specifically illustrating the capillary of the capillary electrophoresis device.
Figure 8:
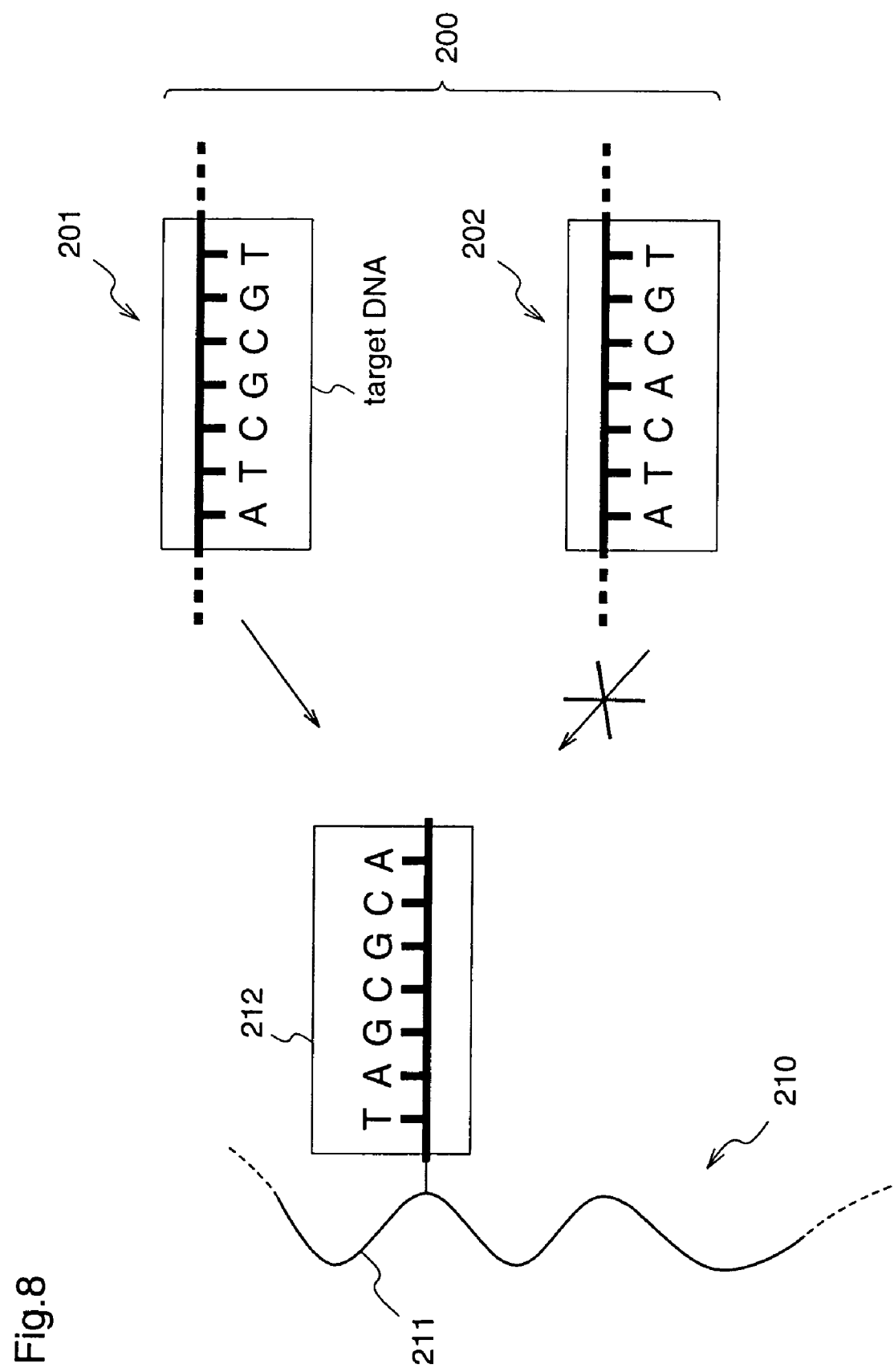
FIG. 8 is a diagram illustrating the state where the sample DNA is separated by the conventional conjugate DNA.

Thereafter, thus formed presample solution including the first and second DNA complexes 51 and 61 is injected by 1 cm to an end of the capillary tube 130 which is previously filled with the conjugate DNA 10 including the buffer solution 11, as shown in FIG. 7.

Then, the both ends of the capillary tube 130 are immersed in the first and second containers 131 and 132 which hold the buffer solution 11 that is adjusted so as to have 50 µmM of TB buffer and 500 µM of magnesium chloride, and further, the positive electrode 133 and the negative electrode 134 are immersed in the buffer solution 11 stored in the containers 131 and 132.

A voltage of 15 kV is applied across the positive electrode 133 and the negative electrode 134 from the variable power supply 135, whereby the first and second DNA complexes 51 and 61 are made to perform electrophoresis at a measurement temperature of 25° C.

Thereby, the first DNA complex 51 and the second DNA complex 61 move in the conjugate DNA 10 that is filled in the capillary tube 130.

Due to the movements of the DNA complexes, the marker DNA 2 of the conjugate DNA 10 is bonded to the second probe 32 of the first ligand DNA 3 in the first DNA complex 51 or to the fourth probe 42 of the second ligand DNA 4 in the second DNA complex 61, and a difference in movements occurs between the first DNA complex 51 and the second DNA complex 61 due to a difference in bonding forces, and therefore, the first and second DNA complexes 51 and 61 can be separated from each other.

Detection of the separated sample DNA is performed as follows. The first sample DNA 5 or the second sample DNA 6 is labeled with a fluorescence dye (FITC), 488 nm of excitation light is emitted from the laser 151 to irradiate the sample DNA with the light, and 520 nm of luminescence emitted from the labeled sample DNA is detected by the photomultiplier 154.

If the method of detecting the DNA itself is adopted when performing detection of the separated sample DNA, since both of the first ligand DNA 3 and the second ligand DNA 4 are included in the presample solution in this first embodiment, a waveform indicating that the two kinds of DNAs are separated is always detected, and therefore, a correct result cannot be obtained. However, when the sample DNA is labeled with the fluorescence dye as described above, only the sample DNA can be detected by detecting the luminescence emitted from the fluorescence dye.

To be specific, the amount of light is controlled by the slit 152, the 488 nm of excitation light emitted from the laser is cut by the filter 153 to remove the same, the 520 nm of luminescence emitted from the sample DNA is detected by the photomultiplier 154 and amplified by the preamplifier 155, and thus obtained signal is digital converted by the A/D converter 156 and captured into the controller 140. Since the detector 150 detects only the fluorescence material that is labeled to the first sample DNA 5 or the second sample DNA 6, excess first ligand DNA 3 or second ligand DNA 4 is not detected. Thereby, a peak of the first DNA complex or the second DNA complex including the ligand DNA 3 or 4, respectively, is detected.

While in the above description one type of sample solution is separated to detect one type of SNPs, it is also possible to separate plural sample solutions at the same time, and detect plural types of SNPs at the same time. In this case, plural types of ligand DNAs corresponding to the plural sample DNAs are prepared by varying the fluorescence dyes for labeling the sample DNAs or varying the lengths of the sample DNAs.

Hereinafter, the result of separation of the first sample DNA and the second sample DNA using the above-mentioned DNA separation method will be described.

It is assumed that the base sequence of the first sample DNA is 5' (FITC)-CGGCTGGGGGCTGA-3', the base sequence of the second sample DNA is 5' (FITC)-CGGT-TGGGGACTGA-3', the base sequence of the marker DNA in the conjugate DNA 10 is 5'-CACGGT-3', the base sequence of the first ligand DNA is 5'-CAGCCCCCAGCCACCGTG-3', and the base sequence of the second ligand DNA is 5'-CAGTCCCCAACCTCGATG-3'. The 3' end of the second ligand DNA 4 may have another base sequence so long as it is not complementary to the marker DNA 2 in the conjugate DNA 10 by at least one base, and does not have a hairpin loop structure.

Figure 2:
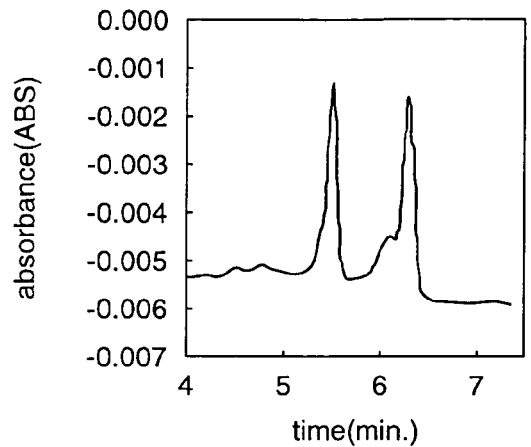
FIG. 2 is a diagram illustrating a separation waveform of the first sample DNA and the second sample DNA in a capillary electrophoresis device according to the present invention.

FIG. 2 is a graph in the case where two types of sample DNAs are included in the sample solution. When two types of sample DNAs are included in the sample solution, since the first and second sample DNAs 5 and 6 that are complementary to the first and second ligand DNAs 3 and 4 are bonded to the ligand DNAs 3 and 4 to form the two types of DNA complexes 51 and 61, respectively, two peaks due to a difference in the electrophoresis speeds are observed.

Of course, either of the above-mentioned two types of sample DNAs may be included in the sample solution. In this case, one peak is observed as shown in FIG. 3 or 4.

Figure 3:
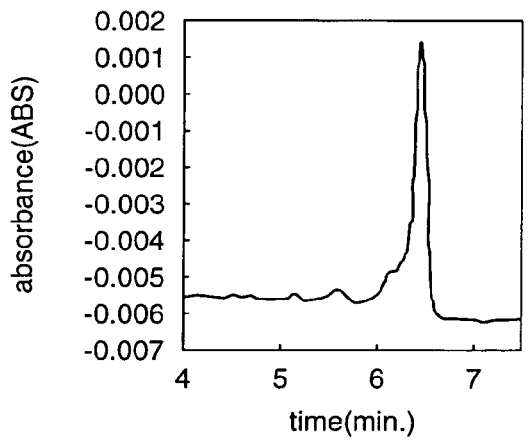
FIG. 3 is a diagram illustrating a waveform of the first sample DNA in the capillary electrophoresis device according to the present invention.

For example, FIG. 3 is a graph in the case where the first sample DNA 5 having a sequence complementary to the first ligand DNA 3 is included in the sample solution. In this case, since only the first ligand DNA 3, the second ligand DNA 4, and the first sample DNA are included in the presample solution, the first sample DNA recognizes a difference in some bases and specifically binds to the first ligand DNA 3 that is completely complementary to the first sample DNA to form only the first DNA complex 51, whereby a single peak is detected as shown in FIG. 3. As a result, specificity of the first ligand DNA is recognized.

Figure 4:
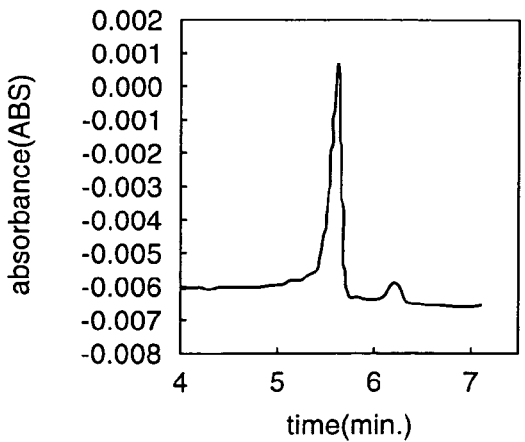
FIG. 4 is a diagram illustrating a waveform of the second sample DNA in the capillary electrophoresis device according to the present invention.

Further, FIG. 4 is a graph in the case where the second sample DNA 6 having a sequence complementary to the second ligand DNA 4 is included in the sample solution. In this case, since only the second sample DNA 6 is included with respect to the first and second ligand DNAs 3 and 4 in the sample solution, the second sample DNA 6 recognizes a difference in some bases and specifically binds to the second ligand DNA 4 having a completely complementary sequence to generate only the second DNA complex 61, whereby a single peak is detected as shown in FIG. 4. As a result, specificity of the second ligand DNA 4 is recognized.

As described above, when both of the first and second ligand DNAs 3 and 4 are included in the presample solution, the sample DNA can be detected even if the sample solution includes at least one of the first and second sample DNAs 5 and 6.

As described above, according to the DNA separation method of the first embodiment, there are prepared the conjugate DNA 10 comprising the non-electrophoresis material 1 and the marker DNA 2, the first ligand DNA 3 including the first probe 31 having a base sequence complementary to the first sample DNA 5 and the second probe 32 having a base sequence complementary to the marker DNA 2 in the conjugate DNA 10, and the second ligand DNA 4 including the third probe 41 having a base sequence complementary to the second sample DNA 6 and the fourth probe 42 having a base sequence that is not complementary to the marker DNA 2 in the conjugate DNA 10 by at least one base. Then, the first sample DNA 5 and the first ligand DNA 3 are hybridized while the second sample DNA 6 and the second ligand DNA 4 are hybridized to form the presample solution including the first and second DNA complexes 51 and 61, and the presample solution is added to the conjugate DNA 10 including the buffer solution to make the first and second DNA complexes 51 and 61 perform electrophoresis. Therefore, the sample DNAs can be separated easily and accurately.

Further, since the ligand DNA comprises a synthetic oligo including the probe having a base sequence complementary to the base sequence of the sample DNA and the probe having a base sequence complementary to the base sequence of the marker DNA in the conjugate DNA, the base sequence of the marker DNA 2 is not varied for each base sequence of the sample DNA but it can be a common base sequence, whereby the conjugate DNA can be easily produced by mass-production. Further, when detecting separation of DNA, it becomes unnecessary to perform inspection for conditions each time at the device end, whereby the DNA separation device can be simplified.

Figure 5:
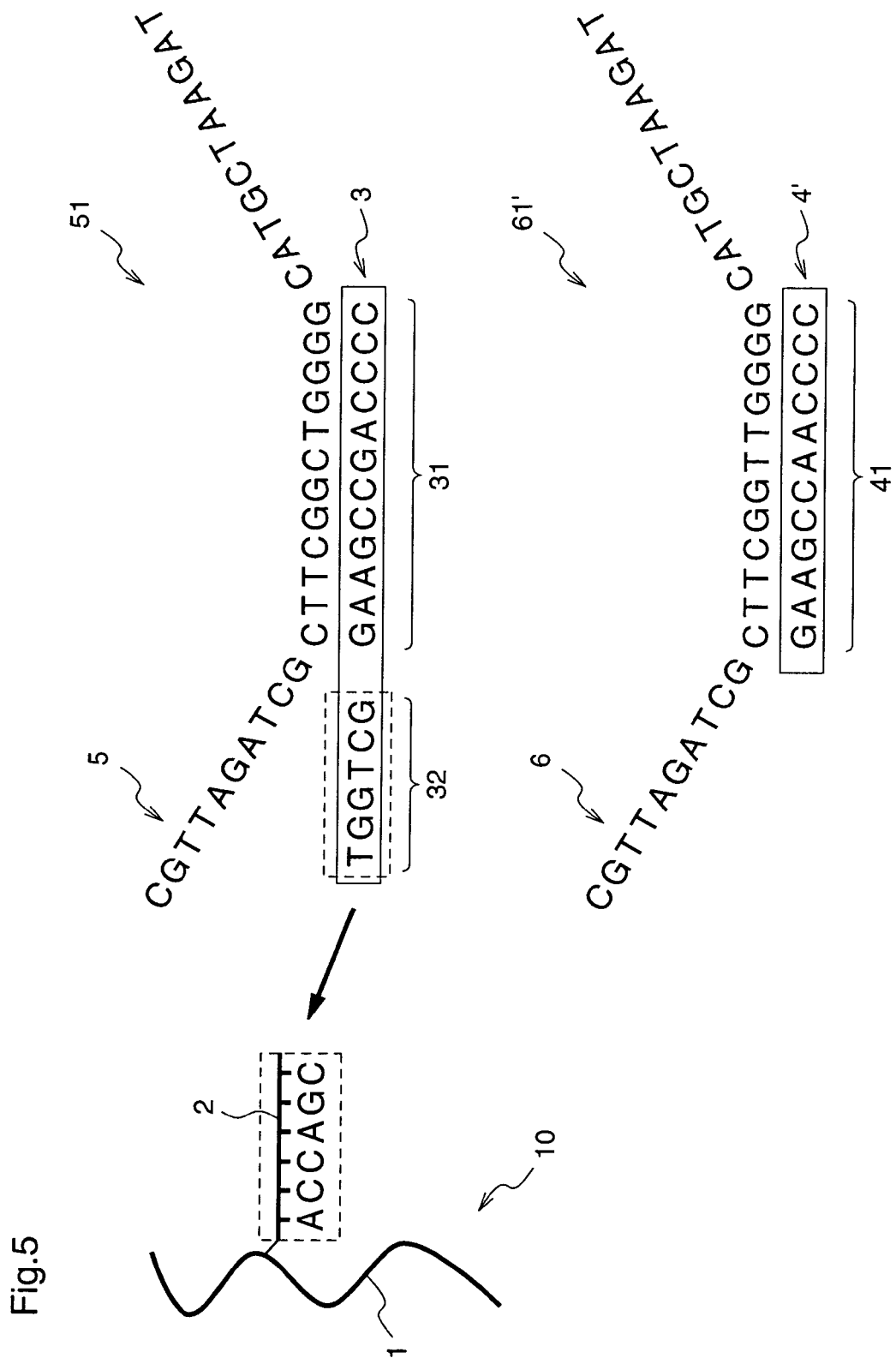
FIG. 5 is a diagram illustrating another examples of correlations between the conjugate DNA, and the first and third DNA complexes comprising the first and third ligand DNAs and the first and second sample DNAs, respectively, according to the firth embodiment of the present invention.

In the description of the first embodiment, the second ligand DNA 4 is a synthetic oligo comprising the third probe 41 having a base sequence complementary to the base sequence of the second sample DNA 6, and the fourth probe 42 having a base sequence that is at least one base different from the base sequence of the second probe 32 in the first ligand DNA. However, a third ligand DNA 4' comprising only the third probe, i.e., having no fourth probe that binds to the conjugate DNA, may be used instead of the second ligand DNA 4, as shown in FIG. 5. In this case, as shown in FIG. 5, the third ligand DNA 4' and the second sample DNA 6 are bonded to form a third DNA complex 61', and the first DNA complex 51 and the third DNA complex 61' are made to perform electrophoresis in the conjugate DNA to separate them, whereby the same effects as mentioned above can be obtained.

APPLICABILITY IN INDUSTRY

A DNA separation device according to the present invention can provide materials which are simple and suited to the intended use when investigating the states of biologic materials by electrophoresis, and it is useful for simplification of the device.

SEQUENCE LISTING

<160> NUMBER OF SEQ ID NOS: 15

<210> SEQ ID NO 1
<211> LENGTH: 7
<212> TYPE: DNA
<213> ORGANISM: Homo sapiens

<400> SEQUENCE: 1 atcgcgt                                                           7

<210> SEQ ID NO 2
<211> LENGTH: 7
<212> TYPE: DNA
<213> ORGANISM: Homo sapiens

<400> SEQUENCE: 2 acgcgat                                                           7

<210> SEQ ID NO 3
<211> LENGTH: 7
<212> TYPE: DNA
<213> ORGANISM: Homo sapiens

```
<400> SEQUENCE: 3 atcgcgt                                                                7

<210> SEQ ID NO 4
<211> LENGTH: 7
<212> TYPE: DNA
<213> ORGANISM: Homo sapiens

<400> SEQUENCE: 4 atcacgt                                                                7

<210> SEQ ID NO 5
<211> LENGTH: 7
<212> TYPE: DNA
<213> ORGANISM: Homo sapiens

<400> SEQUENCE: 5 acgcgat                                                                7

<210> SEQ ID NO 6
<211> LENGTH: 6
<212> TYPE: DNA
<213> ORGANISM: Homo sapiens

<400> SEQUENCE: 6 accagc                                                                 6

<210> SEQ ID NO 7
<211> LENGTH: 12
<212> TYPE: DNA
<213> ORGANISM: Homo sapiens

<400> SEQUENCE: 7 cttcggctgggg                                                          12

<210> SEQ ID NO 8
<211> LENGTH: 12
<212> TYPE: DNA
<213> ORGANISM: Homo sapiens

<400> SEQUENCE: 8 cttcggttgggg                                                          12

<210> SEQ ID NO 9
<211> LENGTH: 18
<212> TYPE: DNA
<213> ORGANISM: Homo sapiens

<400> SEQUENCE: 9 ccccagccgaaggctggt                                                    18

<210> SEQ ID NO 10
<211> LENGTH: 18
<212> TYPE: DNA
<213> ORGANISM: Homo sapiens

<400> SEQUENCE: 10 ccccaaccgaagggcaat                                                    18

<210> SEQ ID NO 11
<211> LENGTH: 14
<212> TYPE: DNA
<213> ORGANISM: Homo sapiens
```

```
<400> SEQUENCE: 11 cggctgggggctga                                                    14

<210> SEQ ID NO 12
<211> LENGTH: 14
<212> TYPE: DNA
<213> ORGANISM: Homo sapiens

<400> SEQUENCE: 12 cggttggggactga                                                    14

<210> SEQ ID NO 13
<211> LENGTH: 6
<212> TYPE: DNA
<213> ORGANISM: Homo sapiens

<400> SEQUENCE: 13 cacggt                                                             6

<210> SEQ ID NO 14
<211> LENGTH: 18
<212> TYPE: DNA
<213> ORGANISM: Homo sapiens

<400> SEQUENCE: 14 cagcccccagccaccgtg                                                18

<210> SEQ ID NO 15
<211> LENGTH: 18
<212> TYPE: DNA
<213> ORGANISM: Homo sapiens

<400> SEQUENCE: 15 cagtccccaacctcgatg                                                18
```

What is claimed is:

1. A DNA separation device for separating, by electrophoresis, a first sample DNA including a first base sequence, and a second sample DNA including a second base sequence that is partially different from the first base sequence, which are contained in a sample solution, wherein a positive electrode and a negative electrode are provided on end portions at both ends of a capillary type hermetically-sealed flow path, respectively, so that the electrodes are immersed in a buffer solution;

a conjugate DNA solution which is obtained by adding, in a buffer solution, a conjugate DNA that is obtained by combining a marker DNA having a specific base sequence with a non-electrophoresis material which performs electrophoresis at a speed that is negligible low relative to the electrophoresis speeds of the first sample DNA and the second sample DNA, is filled in the hermetically-sealed flow path;

a presample solution including a first DNA complex which is obtained by combining the first sample DNA with a first ligand DNA that includes a first probe having a base sequence complementary to the first base sequence, and a second probe having a base sequence complementary to the base sequence of the marker DNA, and a second DNA complex which is obtained by combining the second sample DNA with a second ligand DNA that includes a third probe having a base sequence complementary to the second base sequence, and a fourth probe having a base sequence that is at least one base different from the base sequence of the second probe, is injected into the hermetically-sealed flow path; and voltage is applied to the positive electrode and the negative electrode to make the first DNA complex and the second DNA complex perform electrophoresis in the conjugate DNA solution, thereby separating the DNA complexes.

2. A DNA separation device as defined in claim 1 further including:

a detector for detecting at least one of the first sample DNA and the second sample DNA which move in the hermetically-sealed flow path by electrophoresis;

wherein the conjugate DNA solution is filled in the hermetically-sealed flow path, and the presample solution including at least one of the first DNA complex and the second DNA complex is injected into the hermetically-sealed flow path; and voltage is applied to the positive electrode and the negative electrode to make the first DNA complex or the second DNA complex included in the presample solution perform electrophoresis in the conjugate DNA solution, and at least one of the first DNA complex and the second DNA complex is detected by the detector.

3. A DNA separation device as defined in claim 2 wherein a fluorescence dye is applied to the first sample DNA or the second sample DNA.

4. A DNA separation device as defined in claim 1 wherein each of the first probe and the third probe comprises ten bases or more.

5. A DNA separation device as defined in claim 1 wherein the second probe or the fourth probe comprises six bases or more.

6. A DNA separation device as defined in claim 1 wherein said buffer solution is one selected from a group consisting of a TB buffer solution, a Tris-HCl buffer solution, a TAE buffer solution, and a TBE buffer solution.

7. A DNA separation device as defined in claim 1 wherein said non-electrophoresis material is a linear polymer made of acrylamide or ethylene glycol.

8. A DNA separation method for separating, by electrophoresis, a first sample DNA including a first base sequence, and a second sample DNA including a second base sequence that is partially different from the first base sequence, which are contained in a sample solution, said method comprising:

a filling step of filling a hermetically-sealed flow path with a conjugate DNA solution which is obtained by adding, in a buffer solution, a conjugate DNA that is obtained by combining a marker DNA with a non-electrophoresis material which performs electrophoresis at a speed that is negligible low relative to the electrophoresis speeds of the first sample DNA and the second sample DNA;

a presample solution formation step of mixing and hybridizing the sample solution with a first ligand DNA that includes a first probe having a base sequence complementary to the first base sequence, and a second probe having a base sequence different from the first and second base sequences, and a second ligand DNA that includes a third probe having a base sequence complementary to the second base sequence, and a fourth probe having a base sequence that is at least one base different from the base sequence of the second probe, thereby forming a presample solution including a first DNA complex obtained by combining the first sample DNA with the first ligand DNA, and a second DNA complex obtained by combining the second sample DNA with the second ligand DNA;

an injection step of injecting the presample solution formed in the presample solution formation step into the hermetically-sealed flow path that is filled with the conjugate DNA solution in the filling step; and a separation step of applying a predetermined voltage to a positive electrode and a negative electrode disposed at both ends of the hermetically-sealed flow path to make the first DNA complex and the second DNA complex perform electrophoresis, thereby separating the DNA complexes.

9. A DNA separation method as defined in claim 8 comprising:

said presample solution formation step of mixing and hybridizing the first ligand DNA, the second ligand DNA, and the sample solution including at least one of the first sample DNA and the second sample DNA, thereby forming a presample solution including at least one of the first DNA complex and the second DNA complex;

said injection step of injecting the presample solution into the hermetically-sealed flow path filled with the conjugate DNA solution; and a detection step of applying a predetermined voltage to the positive electrode and the negative electrode to make the first DNA complex or the second DNA complex included in the presample solution perform electrophoresis in the conjugate DNA solution, and detecting at least one of the first DNA complex and the second DNA complex that move in the hermetically-sealed flow path.

* * * * *

UNITED STATES PATENT AND TRADEMARK OFFICE
CERTIFICATE OF CORRECTION

PATENT NO. : 7,887,690 B2  
APPLICATION NO. : 11/585939  
DATED : February 15, 2011  
INVENTOR(S) : Miho Hayashi et al.

Page 1 of 1

It is certified that error appears in the above-identified patent and that said Letters Patent is hereby corrected as shown below:

Title page, item (73) Assignee: should read as follows: Panasonic Corporation, Osaka (JP)

Riken, Saitama (JP)

Signed and Sealed this
Twenty-first Day of February, 2012

David J. Kappos
*Director of the United States Patent and Trademark Office*